(12) United States Patent
Rising et al.

(10) Patent No.: US 7,977,044 B2
(45) Date of Patent: Jul. 12, 2011

(54) RAPID DISSOLVE MEDIA

(75) Inventors: Peter E. Rising, Brightwaters, NY (US);
Brian H. Rutledge, Eldersburg, MD (US); Barbara Walton, Sykesville, MD (US)

(73) Assignee: Industrial Municipal Equipment, Inc., Eldersburg, MD (US)

( * ) Notice: Subject to any disclaimer, the term of this patent is extended or adjusted under 35 U.S.C. 154(b) by 30 days.

(21) Appl. No.: 12/278,184

(22) PCT Filed: Feb. 5, 2007

(86) PCT No.: PCT/US2007/003049
§ 371 (c)(1),
(2), (4) Date: Aug. 4, 2009

(87) PCT Pub. No.: WO2007/092389
PCT Pub. Date: Aug. 16, 2007

(65) Prior Publication Data
US 2009/0291501 A1 Nov. 26, 2009

Related U.S. Application Data

(60) Provisional application No. 60/764,959, filed on Feb. 3, 2006.

(51) Int. Cl.
*C12Q 1/00* (2006.01)
(52) U.S. Cl. .......................................................... 435/4
(58) Field of Classification Search ........................ None
See application file for complete search history.

(56) References Cited

U.S. PATENT DOCUMENTS 581,847 A * 5/1897 Carver ............................. 86/31
6,053,220 A * 4/2000 Lo et al. ........................ 141/129

* cited by examiner

*Primary Examiner* — Mary Lynn Theisen
(74) *Attorney, Agent, or Firm* — F. Chau & Associates, LLC; Nathaniel T. Wallace, Esq.

(57) ABSTRACT

A method for producing a pelletized material includes mixing a media powder with a treated water, the treated water comprising a additive for substantially preventing bacterial contamination, pouring a mixture of the media powder and halogenated water on a non-binding surface, spreading the mixture into a wafer, drying the mixture, and grinding the mixture to produce the pelletized material.

3 Claims, 2 Drawing Sheets

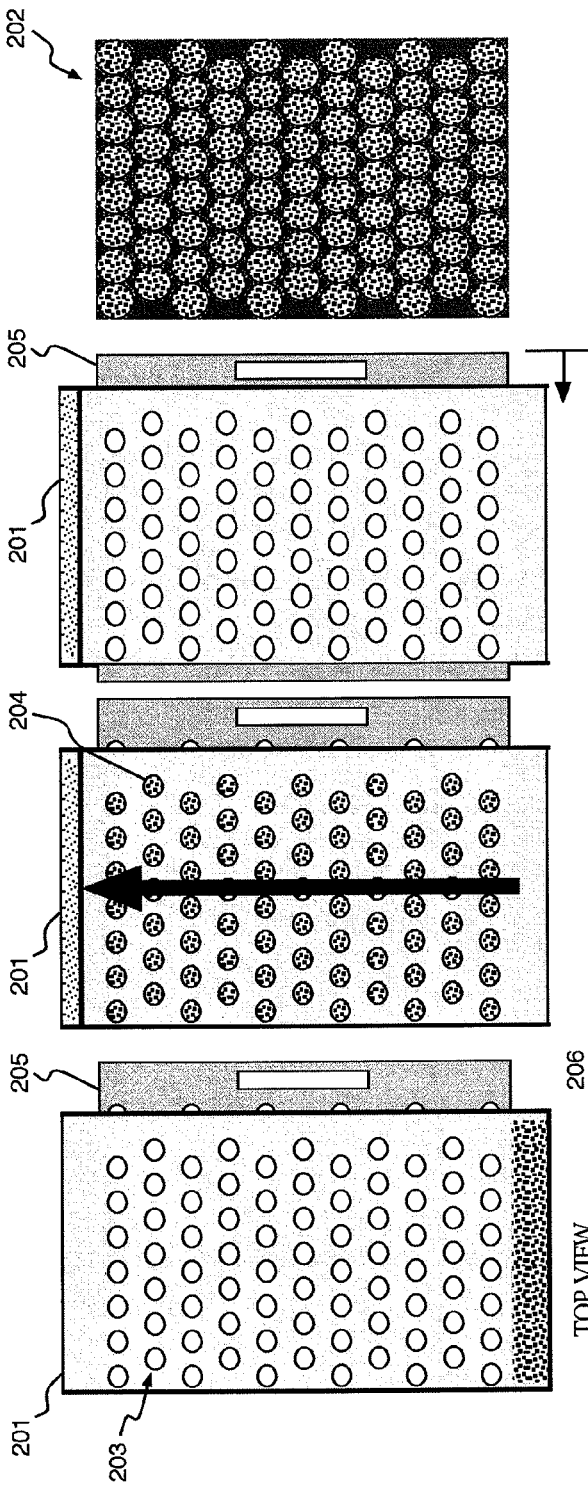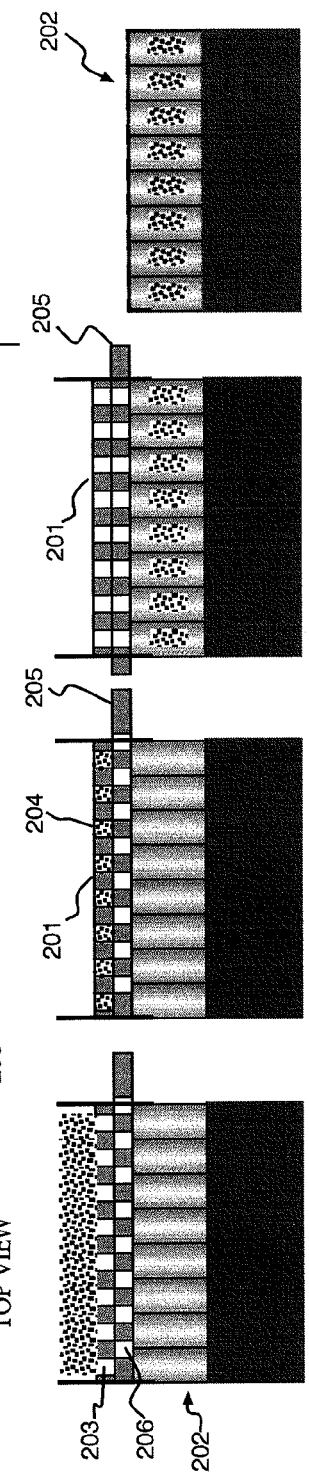

RAPID DISSOLVE MEDIA

CROSS-REFERENCE TO RELATED APPLICATIONS

This application claims priority to International Application PCT/US2007/003049, filed on Feb. 5, 2007 in the U.S. Receiving Office, which claims the benefit of U.S. Provisional Application Ser. No. 60/764,959, filed on Feb. 3, 2006, which are herein incorporated by reference in their entirety.

BACKGROUND OF THE INVENTION

1. Technical Field

The present invention relates to chemical/biological assays, and more particularly to a rapid dissolve media for testing aqueous samples.

2. Discussion of Related Art

Available reagents for testing for the presence of microbial agents are dry powders. These dry powders have certain characteristic dissolving and off-gassing properties.

Some solutions to be tested contain high amounts of dissolved solids such as salts and protein contained in human urine specimens. Another problem is that the solutions to be tested may need to be chilled to preserve microbiologic profile by slowing microbial replication rates. In such cases, the dissolving of a fixed amount of standard media powders such as TSB in a fixed volume of liquid can take longer than the time needed for starting an analysis. Unless dissolved, methods for properly measuring the sample solution may be compromised because the undissolved media acts as a barrier to light transmittance by forming a clump of undissolved media.

Therefore, a need exists for a reagent having improved dissolving and off-gassing characteristics.

SUMMARY OF THE INVENTION

According to an embodiment of the present disclosure, a method for producing a pelletized material includes mixing a media powder with a treated water, the treated water comprising a additive for substantially preventing bacterial contamination, pouring a mixture of the media powder and halogenated water on a non-binding surface, spreading the mixture into a wafer, drying the mixture, and grinding the mixture to produce the pelletized material.

According to an embodiment of the present disclosure, a pelletized material includes a triptic-soy broth powder that dissolves in less than about one minute.

According to an embodiment of the present disclosure, a system for dosing a plurality of ampoules includes a tray disposed above the plurality of ampoules, the tray comprising a first plurality of holes corresponding to the plurality of ampoules disposed there-beneath, each of the first plurality of holes having a size for receiving a predetermined dose of a material, and a board is disposed between the first plurality of holes and the plurality of ampoules, blocking a bottom of the first plurality of holes, wherein the board is movable in a direction substantially parallel to a plane of the board to clear a space between the first plurality of holes and the plurality of ampoules.

BRIEF DESCRIPTION OF THE DRAWINGS

Preferred embodiments of the present invention will be described below in more detail, with reference to the accompanying drawings:

FIGS. 2Ai-Di are a series of diagrams illustrating an operation of a filler tray according to an embodiment of the present disclosure;

FIGS. 2Aii-Dii are a series of diagrams illustrating an operation of a filler tray showing a side view of FIGS. 2Ai-Di, respectively.

DETAILED DESCRIPTION OF PREFERRED EMBODIMENTS

Figure 1:
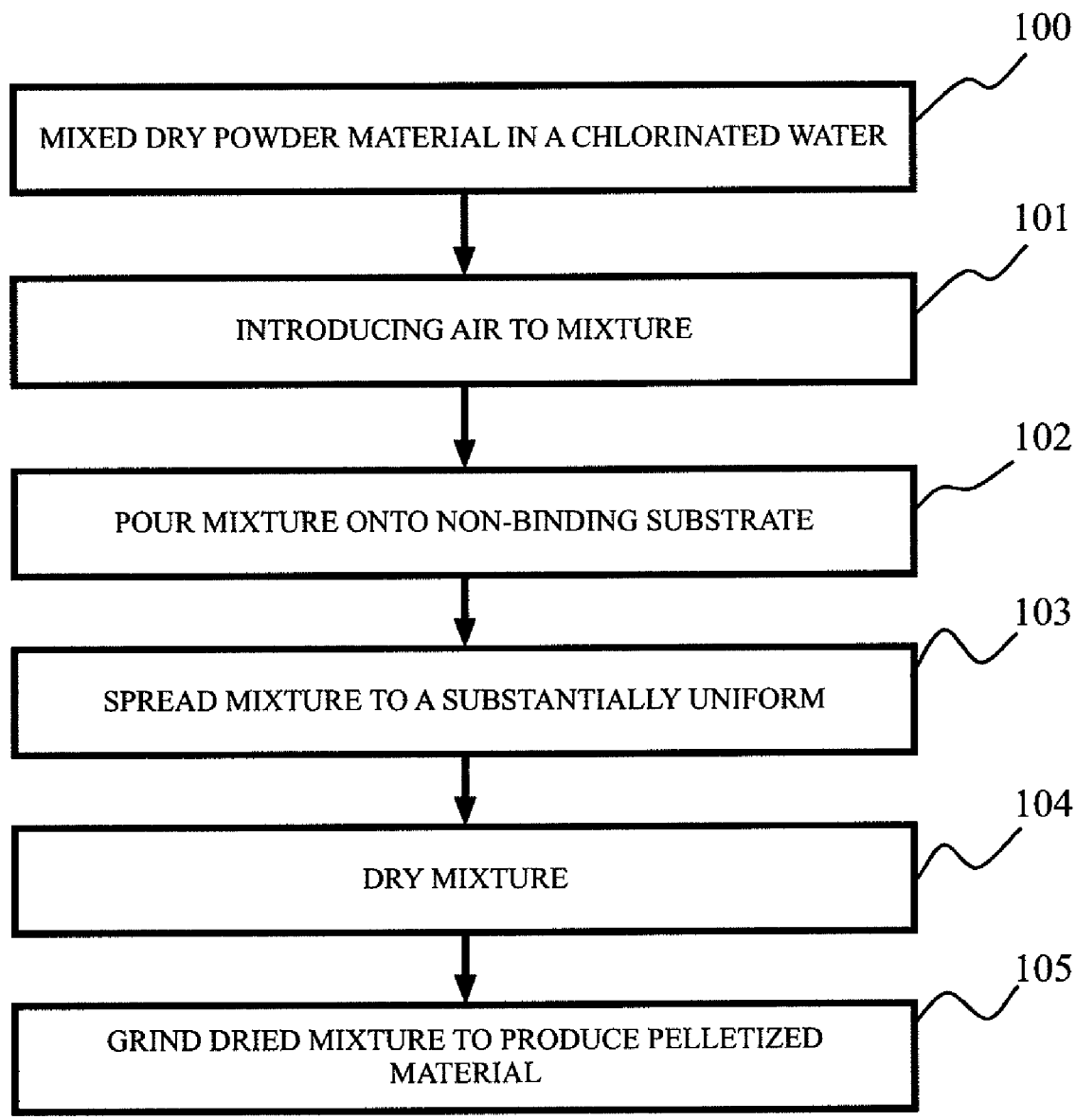
FIG. 1 is a flow chart of a method for manufacturing a palletized material according to an embodiment of the present disclosure.

According to an embodiment of the present disclosure, a dry powder media is reconstituted into a pellet format that possesses improved dissolvability and emits reduced gas while going into solution then the dry powder.

FIG. 1 shows a method for manufacturing a palletized material according to an embodiment of the present disclosure.

Referring to FIG. 1, a media powder, such as commercially available TSB (triptic-soy broth) powder, is mixed with a halogenated (e.g., chlorinated) water (about 0.5 parts-per-million (ppm)) until a paste like material is produced 100. While chlorine is known to impede bacterial growth, at sufficiently low doses bacteria is substantially prevented from contaminating media, e.g., TSB. Iodide or bromine may also be used to reduce the likelihood of media contamination. Additional additives such as other halogens may be used, wherein the additives are water dissolvable. A mixture of media powder and the halogenated water can be prepared without the use binders, mass agents, etc.

A mixing operation is performed 101, e.g., using a high-speed blender, wherein an affective amount of air is entrained into the paste. The air affects drying time and the structure of the resulting pallet and thus dissolving characteristics. Different speeds can be used to produce different characteristics. The mixed material is poured on a non-binding surface such as Teflon®, wax paper, release paper or the like 102. After pouring and before drying can occur, the material is spread into a flat wafer having an average thickness of about 3-10 millimeters (mm) 103 The thickness of 3-10 mm is a wet thickness; the material contracts slightly as it dries. The thickness is selected to balance drying characteristics with pellet size (e.g., thinner spreads yield faster and more consistent drying, while thicker spreads yield larger pellets), such that each pellet is consistently dry. Larger pellets can be dosed more quickly and at less expense than powdered media, for example, powdered media tends to stick to dosing apparatus and clog pipettes and the like.

Once spread, the wafer of TSB paste is dried in a low humidity chamber having about less than 30% relative humidity at a temperature not less than about 70-90 degrees Fahrenheit 104. Further, the temperature is not more than about 74 degrees Fahrenheit. The period of drying is about 1-4 days, e.g., the period of time needed to achieve a consistently dry pellet. After drying the material is ground through a screen mesh (e.g., about 8-40 screen mesh) to produce a pelletized material that has a microbial concentration substantially the same as the dry powder material 105. Pellet material can be prepared having different grain sizes by using different sizes screen meshes.

The pelletized material can be filled into an IME.TEST™ ampoule at a production rate better than about 100 times faster than the dry material.

The pelletized material dissolves in to the test solution better than about 60 times faster than the dry media material.

For example, powdered media takes about 20-30 minutes to dissolve and affects light transmission through the sample as it dissolves. According to an embodiment of the present disclosure, pellets dissolve in less than about 1 minute.

Further, the pelletized material produces approximately half of the off gassing in the ampoule, which is a source of instrument reading distortion.

Further still, as compared to powdered media, pelletized media lessens an affect of the media on light transmission through a sample. For example, as measured using a blank sample (e.g., deionized water) palletized media allows infrared light transmission through a blank sample at about 650-725 lumens. Powdered media allows infrared light transmission through the blank sample at about 500-580 lumens. Accordingly, an impact of a same amount/dose of media is lessened through the pelletization process. By lessening an effect of the media on light transmission a reading of the samples can be more sensitive in lower ranges, e.g., for dark samples such as those containing blood.

Pelletized material also exhibits smaller variations in dosing as compared to powdered material, for example, palletized material achieves dosing within about 50 points, as measured by light transmission through a blank sample, or about 0.1 to 0.12 grams variance among pellets.

The dosing equipment for use with the pellet material includes a plurality of ampoules disposed in an upright arrangement. Referring to FIGS. 2Ai-Di and FIGS. 2Aii-Dii, a tray 201 is disposed above the ampoules 202, the tray 201 comprising a first set of holes 203 corresponding to each ampoule disposed there-beneath (see FIG. 2Ai/ii). The holes have a size adapted to receive a predetermined volume of pellets 204. The first set of holes 203 are in a closed position, e.g., a board 205 is disposed between the first set of holes 203 and the ampoules 202, blocks a bottom of the first set of holes 203. The board 205 includes a second set of holes 206 corresponding the first set of holes 203. Pellets 204 are loaded into each hole 203, filing the first set of holes 203 and preparing a desired dose of the pelletized material (see FIG. 2Bi/ii). After loading each of first set of holes 203 with pellet material the board 205 is moved to align the first and second sets of holes 203 and 206 and a tray of ampoules 202, e.g., 782 ampoules or more, are dosed substantially simultaneously (see FIGS. 2Ci/ii and 2Di/ii). The board need only move a distance equal to about the width of the holes to open the ampoules 202 disposed below.

The filled ampoule is sealed under a vacuum. The vacuum can be relatively strong as the pellet material is dense in comparison to powdered media and is not likely to be sucked out by the vacuum.

The powder material may be dosed prior to drying with a reagent. For example, dosing TSB powder with a reagent such as Triphenyltetrazoliumchloride (TTC). Given an amount of reagent in the mixture, resultant pellets contain a certain amount of reagent.

Different powdered material may be separately processed into different sized pellets. The different sized pellets can be mixed, for example, to achieve different dissolving times, doses, etc.

Having described embodiments for a pelletized material, it is noted that modifications and variations can be made by persons skilled in the art in light of the above teachings. It is therefore to be understood that changes may be made in the particular embodiments of the invention disclosed which are within the scope and spirit of the invention.

What is claimed is:

1. A pelletized material comprising a triptic-soy broth powder that dissolves in less than about one minute.

2. The pelletized material of claim 1, further comprising triphenyltetrazoliumchloride.

3. The pelletized material of claim 1, having a light transmission in a dissolved state in a blank sample greater than a constituent powdered media in a dissolved state in the blank sample.

* * * * *